US00PP16280P2

(12) United States Plant Patent
Brown

(10) Patent No.: US PP16,280 P2
(45) Date of Patent: Feb. 21, 2006

(54) ***THUJA* PLANT NAMED 'WALTER BROWN'**

(50) Latin Name: *Thuja occidentalis*
Varietal Denomination: Walter Brown

(75) Inventor: Walter Brown, South Kingston, RI (US)

(73) Assignee: Spring Meadow Nursery, INC, Grand Haven, MI (US)

( * ) Notice: Subject to any disclaimer, the term of this patent is extended or adjusted under 35 U.S.C. 154(b) by 97 days.

(21) Appl. No.: 10/878,604

(22) Filed: Jun. 28, 2004

(51) Int. Cl.
*A01H 7/00* (2006.01)

(52) U.S. Cl. ..... Plt./213
(58) Field of Classification Search ..... Plt./213
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Thuja* plant named 'Walter Brown', characterized by its broadly pyramidal plant form; yellow-colored leaves when grown under full sun conditions and green-colored leaves when grown in shady conditions; foliage resistant to sun and winter burning; and winter hardy.

1 Drawing Sheet

Botanical classification/cultivar designation: *Thuja occidentalis* cultivar Walter Brown.

BACKGROUND OF THE INVENTION

The present Invention relates to a new and distinct cultivar of *Thuja*, botanically known as *Thuja occidentalis*, and hereinafter referred to by the name 'Walter Brown'.

The new *Thuja* is a naturally-occurring branch mutation of the *Thuja occidentalis* cultivar Techny, not patented. The Inventor discovered the new *Thuja* as a single branch mutation within a population of plants of the parent 'Techny' in a controlled environment in South Kingston, R.I. in 1996.

Asexual reproduction of the new *Thuja* by cuttings in a controlled environment in South Kingston, R.I. since 1999 has shown that the unique features of this new *Thuja* are stable and reproduced true to type in successive generations.

SUMMARY OF THE INVENTION

Plants of the cultivar Walter Brown have not been observed under all possible environmental conditions. The phenotype may vary somewhat with variations in environment and culture such as temperature and light intensity without, however, any variance in genotype.

The following traits have been repeatedly observed and are determined to be the unique characteristics of 'Walter Brown'. These characteristics in combination distinguish 'Walter Brown' as a new and distinct cultivar of *Thuja:*

1. Broadly pyramidal plant form.
2. Yellow-colored leaves when grown under full sun conditions and green-colored leaves when grown in shady conditions.
3. Foliage resistant to sun and winter burning.
4. Winter hardy.

Plants of the new *Thuja* are most similar to plants of the parent, the cultivar Techny. Plants of the new *Thuja* differ primarily from plants of the cultivar Techny in foliage color as plants of the cultivar Techny have blue green-colored foliage.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Thuja.*

The photograph at the top of the sheet is a close-up view of the foliage of a typical plant of 'Walter Brown' grown in the landscape.

The photograph at the bottom of the sheet comprises a side perspective view of a typical plant of 'Walter Brown' grown in the landscape.

DETAILED BOTANICAL DESCRIPTION

Plants used for the aforementioned photographs and following observations and measurements were grown in Grand Haven, Mich., during the summer in an outdoor nursery and under conditions which approximate commercial *Thuja* production. Plants had been growing for about five years when the photographs and description were taken.

In the following description, color references are made to The Royal Horticultural Society Colour Chart, 1995 Edition, except where general terms of ordinary dictionary significance are used.

Botanical classification: *Thuja occidentalis* cultivar Walter Brown.

Parentage: Naturally-occurring branch mutation of the *Thuja occidentalis* cultivar Techny, not patented.

Propagation:

*Type.*—By cuttings.

*Time to initiate roots.*—About 20 days at 20° C.

*Time to produce a rooted cutting.*—About two months at 20° C.

*Root description.*—Thick; creamy white in color.

*Rooting habit.*—Freely branching; dense.

Plant description:

*Form.*—Broadly pyramidal perennial evergreen tree.

*Branching habit.*—Freely branching with branches horizontal to arching, branchlets borne in the same plane, loosely pendulous towards the apices. Trees maintain their lower branches and foliage to the soil level.

*Plant height.*—About 1.5 meters.

*Plant diameter.*—About 1 meter.

*Main stem (trunk) description.*—Height: About 1.2 meters. Diameter: About 3.2 cm. Texture: Woody, flaky. Color: 177B.

*Branch description.*—Length: About 42 cm. Diameter: About 5 mm. Texture: Smooth. Color: 177B.

*Branchlet description.*—Length: About 15 cm. Diameter: About 2 mm. Texture: Scaly. Color: 152B.

*Leaf description.*—Appearance/arrangement: Flattened and appressed; opposite. Length: About 1 mm. Width: About 0.5 mm. Shape: Ovate to lanceolate. Apex: Abruptly pointed. Base: Obtuse. Margin: Entire. Venation pattern: Linear. Fragrance: Cedar-like. Color: Developing leaves, upper surface: 13A. Developing leaves, lower surface: 153A. Fully expanded leaves, upper surface: In full sunlight, 13A; in shade, 153A. Foliage resistant to sun and winter burning. Fully expanded leaves, lower surface: 135A. Venation, upper and lower surfaces: Same as lamina.

Cone description: Cone development has not been observed.

Disease/pest resistance: Plants of the new *Thuja* have not been noted to be resistant to pathogens or pests common to *Thujas.*

Weather tolerance: Plants of the new *Thuja* have been observed to be tolerant to drought, rain, wind and temperatures ranging from −25 to 30° C.

It is claimed:

1. A new and distinct cultivar of *Thuja* plant named 'Walter Brown', as illustrated and described.

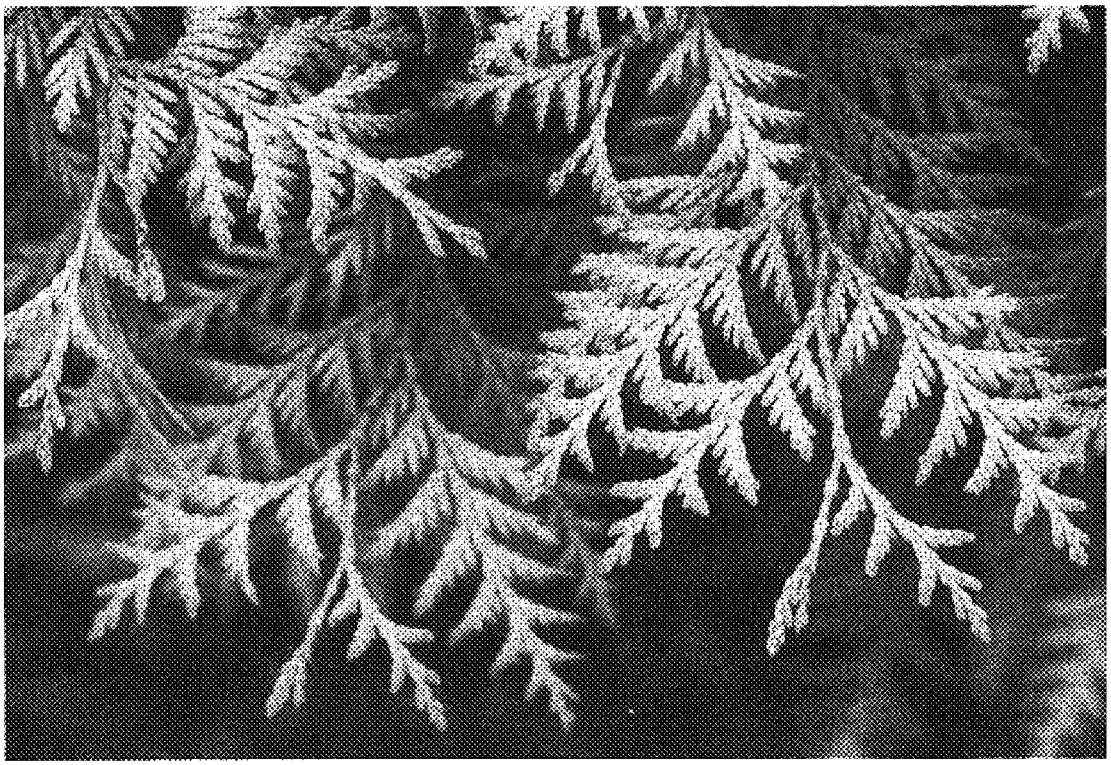
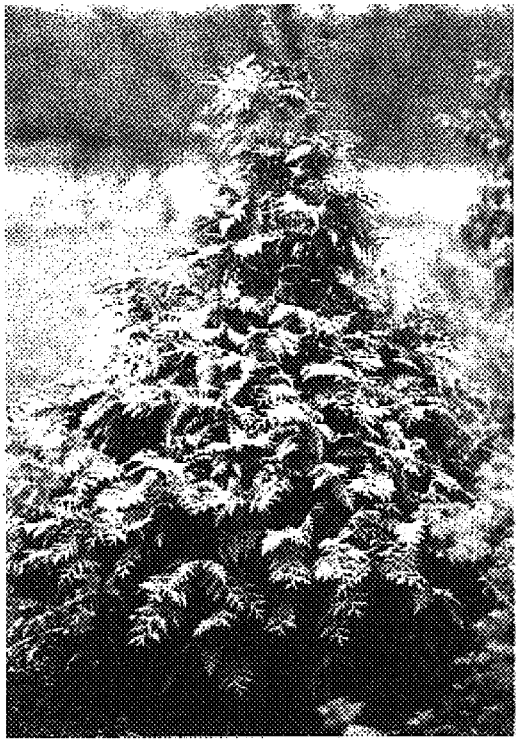

* * * * *